(12) United States Patent
Bowman et al.

(10) Patent No.: US 7,575,596 B2
(45) Date of Patent: Aug. 18, 2009

(54) TWO-LAYER EXTERNAL BREAST PROSTHESIS WITH SELF-SHAPING FEATURE AND PROCESS FOR THE MANUFACTURE THEREOF

(75) Inventors: Roy Wade Bowman, Cumming, GA (US); Robert James Halley, Decatur, GA (US); Lisa Marie Hughey, Marietta, GA (US); Larry Dale Prosser, Jr., Douglasville, GA (US)

(73) Assignee: Amoena Medizin-Orthopädie-Technik GmbH (DE)

( * ) Notice: Subject to any disclaimer, the term of this patent is extended or adjusted under 35 U.S.C. 154(b) by 294 days.

(21) Appl. No.: 10/081,116

(22) Filed: Feb. 21, 2002

(65) Prior Publication Data

US 2002/0193878 A1    Dec. 19, 2002

Related U.S. Application Data (60) Provisional application No. 60/270,382, filed on Feb. 21, 2001.

(51) Int. Cl.
- A61F 2/52 (2006.01)
- B29C 28/00 (2006.01)
- B29C 47/00 (2006.01)
- A63B 39/00 (2006.01)

(52) U.S. Cl. ............... 623/7; 623/8; 156/145; 156/245; 264/101

(58) Field of Classification Search .......... 623/7, 623/8, 11.11, 23.64, 901; 156/145, 245; 264/101

See application file for complete search history.

(56) References Cited

U.S. PATENT DOCUMENTS

| | | | |
|---|---|---|---|
| 2,066,503 A | 1/1937 | Wiggers | |
| 2,580,264 A | 12/1951 | Wright et al. | |
| 3,663,968 A * | 5/1972 | Mohl et al. | 623/7 |
| 3,681,787 A | 8/1972 | Perras | 623/8 |
| 3,795,921 A | 3/1974 | Zucker | 3/36 |
| 3,852,833 A | 12/1974 | Köneke et al. | 3/36 |
| 3,896,506 A | 7/1975 | Hankin | 3/36 |
| 3,934,274 A * | 1/1976 | Hartley, Jr. | 623/8 |
| 4,019,209 A | 4/1977 | Spence | 3/36 |
| 4,086,666 A * | 5/1978 | Vaskys et al. | 623/7 |

(Continued)

FOREIGN PATENT DOCUMENTS

CA    2204490    4/1997

(Continued)

OTHER PUBLICATIONS

"Venetzungssysteme beim Siliconkautschuk," Chemiker-Zeitung 97th year (1973) No. 4, pp. 176-180.

(Continued)

Primary Examiner—Corrine McDermott
Assistant Examiner—Cheryl Miller
(74) Attorney, Agent, or Firm—Ballard Spahr Andrews & Ingersoll, LLP (57) ABSTRACT

A two-layer external breast prosthesis comprising a first inner layer comprised of a self-shaping dispersion and a second outer layer comprised of an elastic material, wherein the second outer layer is relatively stiffer than the first inner layer.

12 Claims, 4 Drawing Sheets

U.S. PATENT DOCUMENTS

| | | | | |
|---|---|---|---|---|
| 4,100,621 | A | | 7/1978 | Ettipio ........................ 2/114 |
| 4,100,627 | A | | 7/1978 | Brill, III ......................... 3/36 |
| 4,125,117 | A | * | 11/1978 | Lee ............................ 450/57 |
| 4,172,298 | A | | 10/1979 | Rechenberg |
| 4,247,351 | A | | 1/1981 | Rechenberg |
| 4,249,975 | A | | 2/1981 | Rechenberg |
| 4,380,569 | A | * | 4/1983 | Shaw ..................... 428/297.4 |
| 4,401,492 | A | | 8/1983 | Pfrommer .................... 156/61 |
| 4,427,351 | A | | 1/1984 | Sano .......................... 418/63 |
| 4,428,082 | A | * | 1/1984 | Naficy ............................ 623/8 |
| 4,528,243 | A | | 7/1985 | Kookootsedes et al. .. 428/425.5 |
| 4,701,230 | A | * | 10/1987 | Loi ............................ 156/145 |
| 4,773,909 | A | * | 9/1988 | Chaglassian ................... 623/8 |
| 4,778,465 | A | | 10/1988 | Wilkins ......................... 623/8 |
| 4,944,749 | A | * | 7/1990 | Becker .......................... 623/8 |
| 4,950,291 | A | | 8/1990 | Mulligan |
| 5,071,433 | A | | 12/1991 | Naestoft et al. |
| 5,141,508 | A | * | 8/1992 | Bark et al. ..................... 623/8 |
| 5,171,321 | A | | 12/1992 | Davis ............................ 623/7 |
| 5,352,307 | A | | 10/1994 | Wild |
| 5,370,688 | A | | 12/1994 | Schulz et al. |
| 5,391,203 | A | | 2/1995 | Bartlett et al. |
| 5,527,359 | A | | 6/1996 | Nakamura et al. ............. 623/7 |
| 5,538,780 | A | | 7/1996 | Pfefermann ................ 428/149 |
| 5,584,883 | A | | 12/1996 | Wild ............................. 623/7 |
| 5,603,791 | A | * | 2/1997 | Weber-Unger et al. ...... 156/145 |
| 5,626,657 | A | | 5/1997 | Pearce ........................ 106/122 |
| 5,738,812 | A | * | 4/1998 | Wild ........................... 264/102 |
| 5,792,292 | A | | 8/1998 | Wild |
| 5,798,062 | A | | 8/1998 | Thielbar ..................... 264/40.1 |
| 5,824,075 | A | | 10/1998 | Thielbar ........................ 623/7 |
| 5,895,423 | A | | 4/1999 | Becker et al. |
| 5,902,335 | A | * | 5/1999 | Snyder, Jr. ..................... 623/7 |
| 5,922,023 | A | | 7/1999 | Mulligan et al. |
| 5,925,282 | A | | 7/1999 | Rasmussen |
| 6,020,055 | A | | 2/2000 | Pearce ........................ 428/323 |
| 6,136,027 | A | | 10/2000 | Jackson ......................... 623/7 |
| 6,162,250 | A | | 12/2000 | Malice et al. |
| 6,197,099 | B1 | | 3/2001 | Pearce ........................ 106/122 |
| 6,296,800 | B1 | | 10/2001 | Stelter et al. ................ 264/267 |
| 6,342,117 | B1 | | 1/2002 | Reitmaier et al. ........... 156/145 |
| 6,443,986 | B1 | | 9/2002 | Malice, Jr. et al. ............. 623/7 |
| 6,494,912 | B2 | | 12/2002 | Reitmaier et al. ............... 623/7 |
| 6,660,204 | B1 | | 12/2003 | Clover, Jr. et al. ........... 264/222 |
| 6,679,912 | B2 | | 1/2004 | Stelter ............................ 623/7 |
| 2002/0073305 | A1 | | 6/2002 | Joseph et al. ................... 713/1 |
| 2002/0099442 | A1 | | 7/2002 | Niino ............................. 623/7 |
| 2002/0103539 | A1 | | 8/2002 | Stelter ............................ 623/7 |
| 2002/0105523 | A1 | | 8/2002 | Behrbaum et al. ........... 345/543 |
| 2002/0193878 | A1 | | 12/2002 | Bowman et al. |
| 2003/0149481 | A1 | | 8/2003 | Guest et al. .................... 623/8 |
| 2003/0208269 | A1 | | 11/2003 | Eaton et al. .................... 623/7 |
| 2003/0224699 | A1 | | 12/2003 | Chen .......................... 450/38 |
| 2004/0010311 | A1 | | 1/2004 | Reynolds et al. |
| 2005/0273164 | A1 | | 12/2005 | Bowman et al. |

FOREIGN PATENT DOCUMENTS

| | | |
|---|---|---|
| DE | 2605148 | 2/1976 |
| EP | 0 768 068 B1 | 6/2001 |
| GB | 662482 | 5/1949 |
| GB | 858878 | 10/1959 |
| GB | 1110479 | 11/1966 |
| WO | WO9517141 | 6/1995 |
| WO | WO97/13478 | 4/1997 |
| WO | WO9925536 | 5/1999 |

OTHER PUBLICATIONS

CD-Rom Video entitled "How a Breast Form is Born" © 1992 Amoena Corp.

US 6,120,250, 09/2000, Durgin et al. (withdrawn)

* cited by examiner

TWO-LAYER EXTERNAL BREAST PROSTHESIS WITH SELF-SHAPING FEATURE AND PROCESS FOR THE MANUFACTURE THEREOF

CROSS REFERENCE TO RELATED APPLICATIONS

The present application claims priority to and the benefit of co-pending U.S. Provisional Patent Application Ser. No. 60/270,382 filed Feb. 21, 2001, the entire text of which is specifically incorporated herein by this reference for all purposes.

FIELD OF THE INVENTION

The invention relates generally to a breast prosthesis. More particularly, the invention relates to a two-layer external breast prosthesis having a first outer layer filled with a relatively firm elastomeric material and inner layer made of a flowable, self-shaping material which is adapted to hold its shape against the chest wall of a patient.

BACKGROUND OF THE INVENTION

A variety of breast prostheses are known. These devices have been developed so that women who have undergone a surgical procedure in which they have had one or possible both breast removed, for example a mastectomy, may restore not only their cosmetic appearance after surgery, but their self-confidence as well. The use of breast prostheses has thus minimized the stigma that may have otherwise been attached to a woman's appearance after breast removal surgery.

One example of a prosthetic breast is disclosed in German Patent No. DE-AS 26 05 148. This prosthesis has a shell shaped component enclosed or enveloped by plastic films, and is made of a two-component silicone rubber material. A cured two-component silicone rubber material is used to form the shell of the prosthesis, which material corresponds in its weight to the approximate weight of natural breast tissue. The two-component silicone rubber material also simulates the actual conditions of a natural breast due to the soft, elastic responsiveness and mobility of the material. Additional breast prostheses of this type, which are intended for being placed in and supported by a brassiere, are disclosed in U.S. Pat. Nos. 4,172,298 and 4,249,975, respectively.

In order to assure the most natural appearance of the breast prosthesis when inserted in the brassiere, a breast prostheses of the type described above may be provided with a first body portion forming the convex exterior side of the prosthesis, this portion being made of a soft set material. In addition, a second and flat shell shaped body portion forms the back or inner side of the prosthesis, which second body portion is made of a slightly harder set two-component silicone rubber material. The result of this design is that the elastically soft material of the first body portion, which due to its weight tends to sink slightly along the convex external side thereof, is supported by the rear or flat shell body portion made of the stiffer material. The disadvantage of this type of prosthesis, however, is due to the fact that as the inner shell is fabricated of a relatively harder or stiffer two-component silicone rubber material, the inner shell will press on the sensitive scar tissue area(s) of the patient's external chest wall. Additionally, the inner shell also does not adjust, i.e., it does not conform, about the scar tissue area(s) in order to protect or cushion those tissues.

The problem persists in that many of the known types of external breast prostheses have not been made adaptable to fit any irregularities that may be present in the chest wall of the mastectomy patient, particularly as modern surgical techniques remove less tissue and leave more irregular chest wall contours. Although matching a patient's chest wall contours has been accomplished by the custom-molding of a prosthesis for each patient, a need exists for a prosthesis that has desirable appearance and touch characteristics, which can adapt to the chest wall contours of a wide variety of women, and can also be made available in a cost-effective manner.

One attempt to satisfy this need is disclosed in U.S. Pat. No. 4,950,291 to Mulligan, the provisions of which are incorporated herein by this reference. The '291 patent discloses a 2-layer breast prosthesis comprised of an outer layer or shell filled with a relatively firm elastomeric silicone gel, and an inner layer of an extremely soft and flowable cross-linked silicone gel. The softer, flowable gel will conform to the chest wall with a minimum of applied force, but does not possess self-molding characteristics such that, for example, the flowable gel does not hold its shape when the prosthesis is removed. Also, due to the fact the inner gel readily flows, the gel can "pool" at times in and along the bottom of the prosthesis due to the influence of gravity, which in turn may lead to patient discomfort and generally does not offer any additional support to the fit and security of the prosthesis. Furthermore, the soft gel-like material disclosed in the '291 patent is of the same density as the outer gel, and can therefore result in a final product, which may be heavier than a comparable single layer prosthesis.

What is needed, but seemingly unavailable in the art, is an improved breast prosthesis that will have the desired outward cosmetic appearance, shape, and feel of a woman's breast, yet will be adaptable to the chest wall of the wearer by forming to the profile thereof. What is also needed is such an improved breast prosthesis which will be lighter than the known prosthetic devices for greater patient comfort during prolonged wear, and which may also be light enough that it will be self-supporting on the chest wall of the wearer. Additionally, there is a need for an improved two-layer breast prosthesis having a relatively firm outer shell component with a relatively soft and compliant inner shell component that will not settle as the prosthesis is worn by a patient.

SUMMARY OF THE INVENTION

Among other aspects, this invention provides an improved and lightweight breast prosthesis comprising two layers, each of which is a shell shaped component. The breast prosthesis has an external component or body portion which mimics the shape of the breast with a hardness correlating to the soft, elastic responsiveness of natural breast tissue, and has an inner component or body portion comprised of a flowable, self-shaping material possessed with an ability to hold its shape.

In contrast to popular belief that the frontal area of the prosthesis must be supported by a rear shell-shaped component of a greater hardness, the breast prosthesis of this invention fabricates this rear component of a relatively softer material. The inner shell shaped component thus is soft enough, due to its consistency, that it is able to adjust to or fit about the scar tissue area(s) of the patient's chest wall without exerting any undue pressure thereon, and to maintain that shape/conformation in the absence of internal shearing forces.

In a first aspect, the present invention provides a two-layer external breast prosthesis comprising a first inner layer comprised of a self-shaping dispersion, the dispersion having a specific gravity of less than 1.0, a second outer layer comprised of an elastic material, wherein the second outer layer is stiffer than the first inner layer.

In a second aspect, the present invention provides a two-layer breast prosthesis comprising a first film envelope configured to define a first interior volume, and a second film envelope joined to the first film envelope along a common side edge to thereby define a second interior volume, wherein the second film envelope and the first film envelope share a common film wall. A first and a second sealed fill opening, respectively, extends from the common side edge of the first film envelope and the second film envelope to the respective first and second interior volumes. A first material positioned within the first film envelope forms an interior body portion of the prosthesis, the first material comprising a self-shaping material. A second material is positioned within the second film envelope for forming an exterior body portion of the prosthesis. The second material comprises an elastic material and/or curable elastic material precursor.

In still a third aspect, the present invention provides a process for manufacturing a two-layer breast prosthesis comprising the steps of providing a first film envelope configured to define a first interior volume, and a second film envelope joined to the first film envelope along a common side edge to thereby define a second interior volume. The second film envelope and the first film envelope share a common interstitial film wall, and both the first and second film envelopes further comprise a respective first and a second fill opening extending from the common side edge of the respective first and second film envelopes to the respective first and second interior volumes. The method also comprises at least partially filling the second interior volume by passing an elastic material and/or curable elastic material precursor through the second fill opening; at least partially filling the first interior volume by passing a self-shaping dispersion through the first fill opening; and sealing the first and second fill openings.

Additional advantages and embodiments of the invention will be obvious from the description, or may be learned by practice of the invention. Further advantages of the invention will also be realized and attained by means of the elements and combinations particularly pointed out in the appended claims. Thus, it is to be understood that both the foregoing general description and the following detailed description are exemplary and explanatory of certain embodiments of the invention and are not restrictive of the invention as claimed.

DETAILED DESCRIPTION

The present invention may be understood more readily by reference to the following detailed description and any examples provided herein. The terminology used herein is used only for the purpose of describing particular embodiments of the present invention and is not intended to be limiting in any way. Furthermore, it must also be noted that, as used in the specification and the appended claims, the singular form "a," "an," and "the" comprise plural referents unless the context clearly indicates otherwise. For example, reference to a component in the singular is intended to comprise a plurality of components.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about" or "approximately", it will be understood that the particular value forms another embodiment. Moreover, it should be understood that throughout this application, where publications are referenced, the disclosures of these publications in their entireties are hereby incorporated by reference into this application in order to more fully describe the state of the art to which this invention pertains.

As indicated above, in a first embodiment, the present invention provides a two-layer external breast prosthesis comprising a first inner layer comprised of a self-shaping dispersion having a specific gravity of less than 1.0, and a second outer layer comprised of an elastic material, wherein the second outer layer is stiffer than the first inner layer. In accordance with this and other embodiments disclosed herein, therefore, the self-shaping dispersion of the first inner layer preferably comprises a dispersion of silicone oil and a plurality of microspheres formulated to provide the desired self-molding or shaping characteristics. In one embodiment, the self-shaping dispersion has a specific gravity of less than 1.0. In another embodiment, the dispersion preferably has a reduced density of 0.4–0.5 (where water has a specific gravity of 1.0), compared to a silicone gel containing no microspheres and having a specific gravity of 1.0. Advantageously, the use of this self-shaping dispersion is capable of providing the desired self-shaping characteristics while reducing the overall weight of the prosthesis.

In an alternate embodiment, it is contemplated that the self-shaping dispersion will be comprised of non-crosslinked material. As a result, the self-shaping material can advantageously be redistributed within the breast prosthesis to accommodate special considerations on the chest wall, such as mounds or voids. Accordingly, the wearability characteristics of the breast prosthesis are substantially improved, and despite the use of a softer, flowable, and formable material and design of the inner shell, the appearance of the breast prosthesis when inserted in the brassiere does not suffer so that the prosthesis retains its natural look.

To this end, in a preferred embodiment, the self-shaping material will comprise a dispersion of microspheres suspended, or dispersed, within a fluid media. It is anticipated that the fluid media will comprise a silicone oil having a viscosity in the range of from approximately 100 CSt to approximately 5000 CSt, including such values as 200, 300, 400, 500, 600, 700, 800, 900, 1000, 2000, 3000, and 4000. In one embodiment, the silicone oil preferably has a viscosity of approximately 500 CSt. To minimize the separation of the dispersed components, i.e., the microspheres, optional additives such as thixotropic agents and stabilizers may also be added to the fluid/dispersion mixture. The fluid media acts as a lubricant which allows the microspheres to shear and flow within the inner layer of the prosthesis when it is received against the patient's chest wall while being worn. After application, in the absence of shearing forces, the weak mechanical interactions of the microspheres create a weak structure which allows the material to maintain its conformation, i.e., its shape. It should be understood that since the self-shaping dispersion is an uncured dispersion, it may separate over time, but can be regenerated by gently kneading the backside of the inner layer of the prosthesis for a few seconds.

In accordance with this and other embodiments that will be described below, it should also be understood that the plurality of microspheres can be comprised of a variety of polymeric substances known to one of ordinary skill in the art, including without limitation, such substances as glass or acrylonitrile copolymers. Examples of available microspheres that may be used in the self-shaping material include the Expancel 091-DE-50; 091-DET-50; 091-DE-80; 091-DET-80 (Akzo-Nobel) and Scotchlite microspheres available from the 3M Company. In one embodiment, the microspheres are preferably comprised of an acrylonitrile copolymer.

In yet another embodiment, it should also be understood that suitable microspheres according to the invention will preferably have an average particle size of between 40 and 125 microns, including such values as 45, 50, 55, 60, 65, 70, 75, 80, 85, 90, 95, 100, 105, 110, 115, and 120 microns. To this end, it is understood that the plurality of microspheres can be hollow and/or gas filled. Such gases include, without limitation, organic gases such as methane, ethane, propane, butane, isobutane and the like, as well as inert gases such as nitrogen and the like. As such, in an alternate embodiment of the present invention, at least a portion of the plurality of microspheres are preferably filled with an isobutane gas.

In view of the foregoing and in accordance with the present invention, a typical formulation of the self-shaping material may thus be comprised of a silicone oil (500 CSt) of 100 pbw, blended with hollow microspheres of 4.5–5.5 pbw. Due to variances in specific gravity and size gradients between microsphere batches, one of ordinary skill in the art will appreciate that the actual blend ratio may vary. The self-shaping dispersion is formulated so that it stands on its own, with a consistency like whipped cream or well beaten egg whites.

As previously indicated, in several alternate embodiments, the self-shaping dispersion may be formulated with the addition of one or more optional rheological additives and/or thixotropes. The addition of the thixotrope increases the time required for the components within the dispersion to separate, which improves processing and therefore reduces the need for the end user to frequently knead the product to re-disperse the components. Non-limiting examples of suitable thixotropes can include Aerosil, available from Degussa; Cab-o-sil, available from the Cabot Corporation; and Wacker HDK, available from Wacker Silicones. Therefore, a typical, non-limiting example in accordance with this embodiment will comprise silicone oil (500 CSt) in the amount of 100 pbw; suitable microspheres in the amount of 2–4 pbw; and Aerosil 200 in the amount of 1–4 pbw (thixotrope).

The second outer layer of the prosthesis is comprised of a relatively stiff elastic material. To this end, the relatively stiffer outer layer of the prosthesis maintains the shape of the breast form and prevents outermost films from wrinkling while at the same time remaining sufficiently soft to yield to the touch. In a preferred embodiment, the elastic material is comprised of a heat cured silicone gel. It is also understood that in an alternate embodiment the outer layer silicone gel can likewise comprise a material of reduced density, and hence a reduced weight through the addition of microspheres.

It will be appreciated that the preparation of the relatively stiff silicone gel based elastic material forming the outer layer of the prosthesis is generally within the expertise of those skilled in the art. An appropriate silicone rubber is described in detail by Patzke and Wohlfarth in their article entitled "Venetzungssysteme beim Siliconkautschuk," published in the CHEMIKER-ZEITUNG $97^{th}$ year (1973) No. 4, pages 176–180. Furthermore, the relative stiffness of the silicone gel material may be selected as desired to attain the advantages described hereinabove. Preferably, the silicone rubber material forming the outer layer will have a penetration measured in a range from 20.0 to 24.0 mm. Such values represent measurements with a "precision" penetrometer using a 15 gram cone having an aluminum tip with a height of 0.6 inches, a base diameter of 0.33 inches, and a plastic cone body extending 1.13 inches from the tip base and having a base diameter of 2.56 inches.

In accordance with this and other embodiments of the present invention, the first inner layer and second outer layer of the two-layer breast prosthesis are each confined within a first film envelope and a second film envelope, respectively. In a preferred embodiment, the first and the second film envelopes share a common, interstitial film wall therebetween. Therefore, in one embodiment, the inner and outer layers of the two-layer prosthesis are separated by this interstitial film wall. To this end, any suitable film composition known to one of ordinary skill in the art can be used with the present invention. However, in a preferred embodiment, the films used to form the respective film envelopes are polyurethane films.

As previously set forth above, in a second aspect, the present invention further provides a two-layer breast prosthesis comprising a first film envelope configured to define a first interior volume, and a second film envelope joined to the first film envelope along a common side edge to thereby define a second interior volume, wherein the second film envelope and the first film envelope share a common film wall. A first and a second sealed fill opening, respectively, which in each embodiment of the invention may comprise a bifurcated fill valve or opening having separate channels passing to each respective body portion of the prosthesis, each extend from the common side edge of the first film envelope and the second film envelope to the respective first and second interior volumes. A first material is placed within the first film envelope forming an interior body portion of the prosthesis, the first material comprising a self-shaping material. A second material is placed within the second film envelope to form an exterior body portion of the prosthesis, the second material comprising an elastic material and/or curable elastic material precursor.

In a third aspect, the present invention provides a process for manufacturing a two-layer breast prosthesis comprising the steps of providing a first film envelope configured to define a first interior volume and a second film envelope joined to the first film envelope along a common side edge to thereby define a second interior volume. The second film envelope and the first film envelope share a common interstitial film wall, and the first and the second film envelopes further comprise a respective first and a second fill opening extending from the common side edge of the respective first and second film envelopes to the respective first and second interior volumes. The process further comprises at least partially filling the second interior volume by passing an elastic material and or curable elastic material precursor through the second fill opening, at least partially filling the first interior volume by passing a self-shaping dispersion through the first fill opening, and thereafter sealing the first and second fill openings.

Referring now to the drawings, in which like reference characters indicate like parts throughout the several views, a breast prosthesis 5 is illustrated. The breast prosthesis is made of a first layer, envelope, chamber, or body portion 7 and a separate second layer, envelope, chamber, or body portion 8. The prosthesis can be manufactured by providing a first plastic film 9 and a second plastic film 12, which are used to form the film envelopes of the prosthesis. A third film 11, an interstitial film is sealably affixed by heat welding or any other means know to one of ordinary skill, between the exterior films 9, 12 and along their respective and common side edges to provide a first and a second film envelope and leaving only a bifurcated fill opening 16 for each respective envelope or chamber and extending from the common side edge of the two film envelopes into the interior volume of the envelopes so fabricated, and which envelopes will become the two body portions of the prosthesis. In accordance with the embodiments described herein, the films 9, 11, and 12 are preferably polyurethane films.

The films are placed in a lower mold half (not illustrated) of one of the known types of molds having a surface design similar to the desired shape of a breast. A two-component soft set silicone gel or other curable elastic material precursor 13 is passed through one conduit of the bifurcated fill opening 16 in the welded films 9 and 11 to thereby at least partially fill the interior volume of the first film envelope, and to also form the convex breast-shaped exterior first body portion of the prosthesis. A self-shaping dispersion or material 15 is passed through a second conduit of the bifurcated fill opening 16 between the films 11 and 12 to thereby at least partially fill the interior volume forming the second layer or body portion of the prosthesis as well as the concave interior side thereof. The aforementioned conduits of the bifurcated fill opening 16, otherwise referred to as the first and the second fill openings in the film envelopes, are then sealed shut, simultaneously or individually, by heat welding or any other means known to one of ordinary skill in the art. The mold is then closed about the formed prosthesis by an upper mold component (not illustrated) whose shape corresponds with the rear or back side of the prosthesis, and heat is applied to the mold which causes the film to form to the desired breast form shape, and cures the silicone gel in the first or exterior body portion of the prosthesis.

Figure 1:
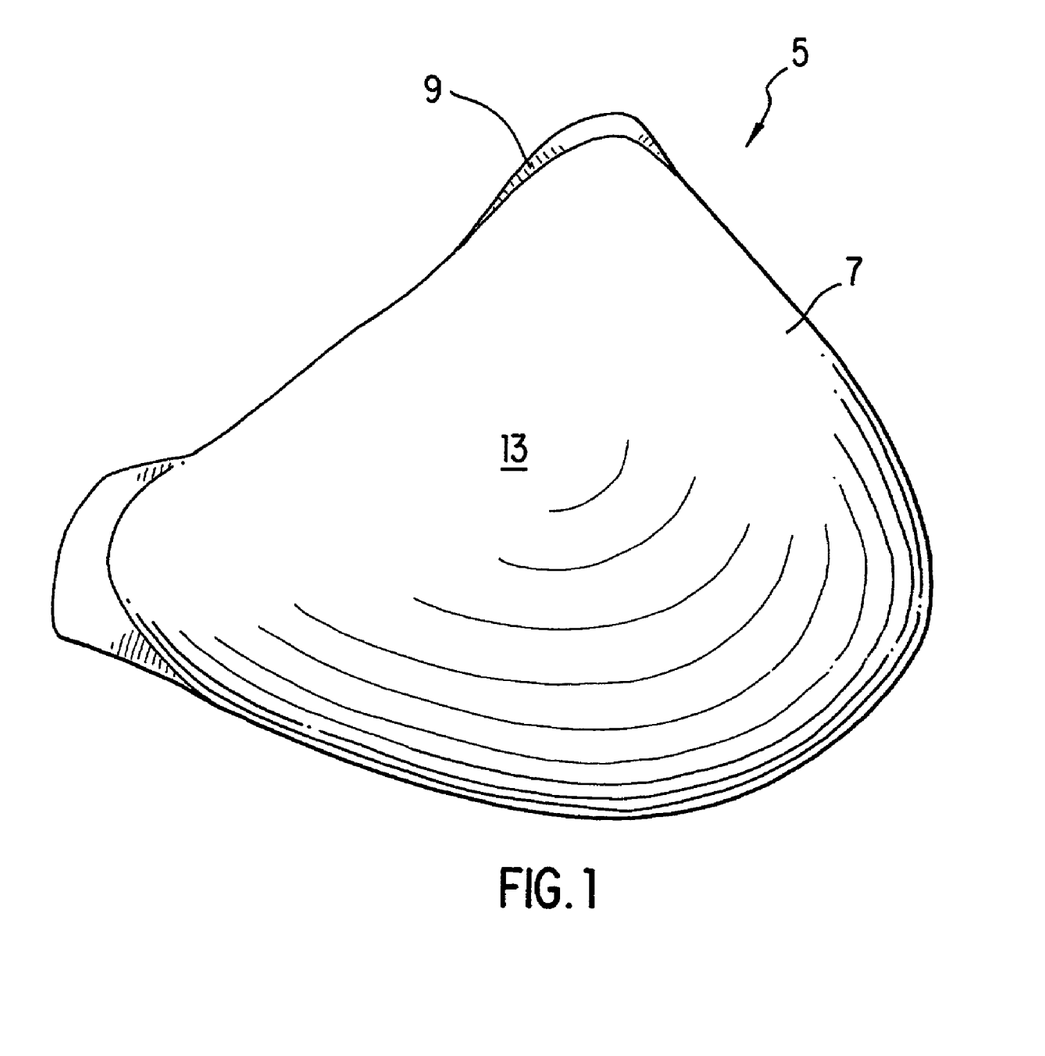
FIG. 1 is a front or top plan view of a breast prosthesis embodying the present invention, illustrating the first body portion thereof.
Figure 2:
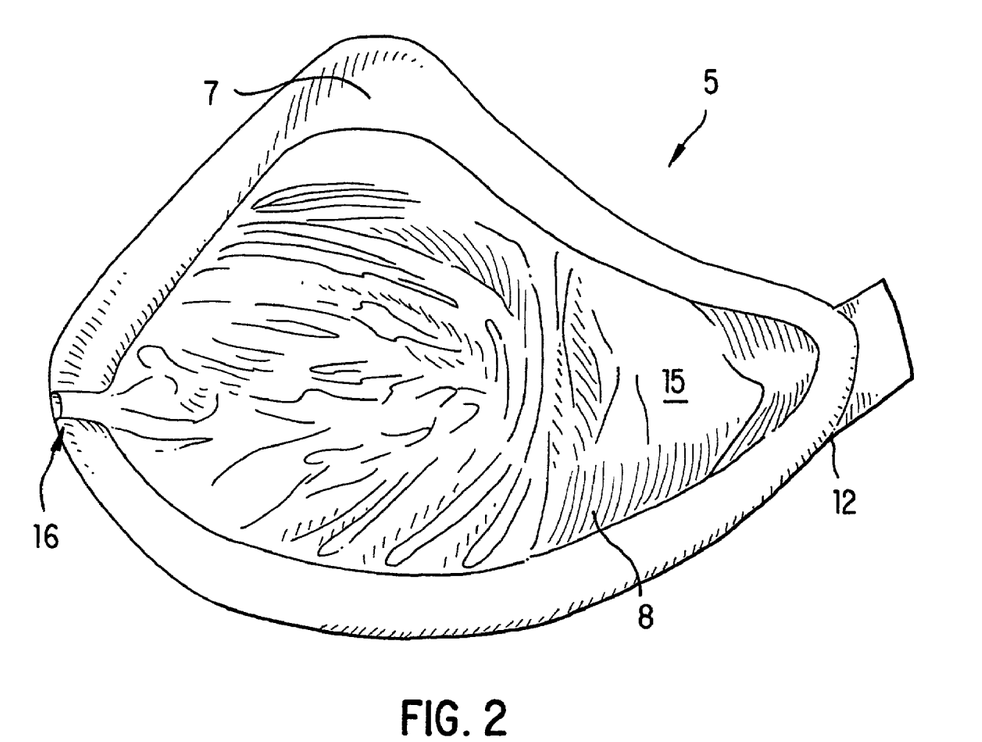
FIG. 2 is a rear or bottom plan view, in partial perspective, of the prosthesis of FIG. 1, illustrating the second self-shaping body portion thereof.
Figure 3:
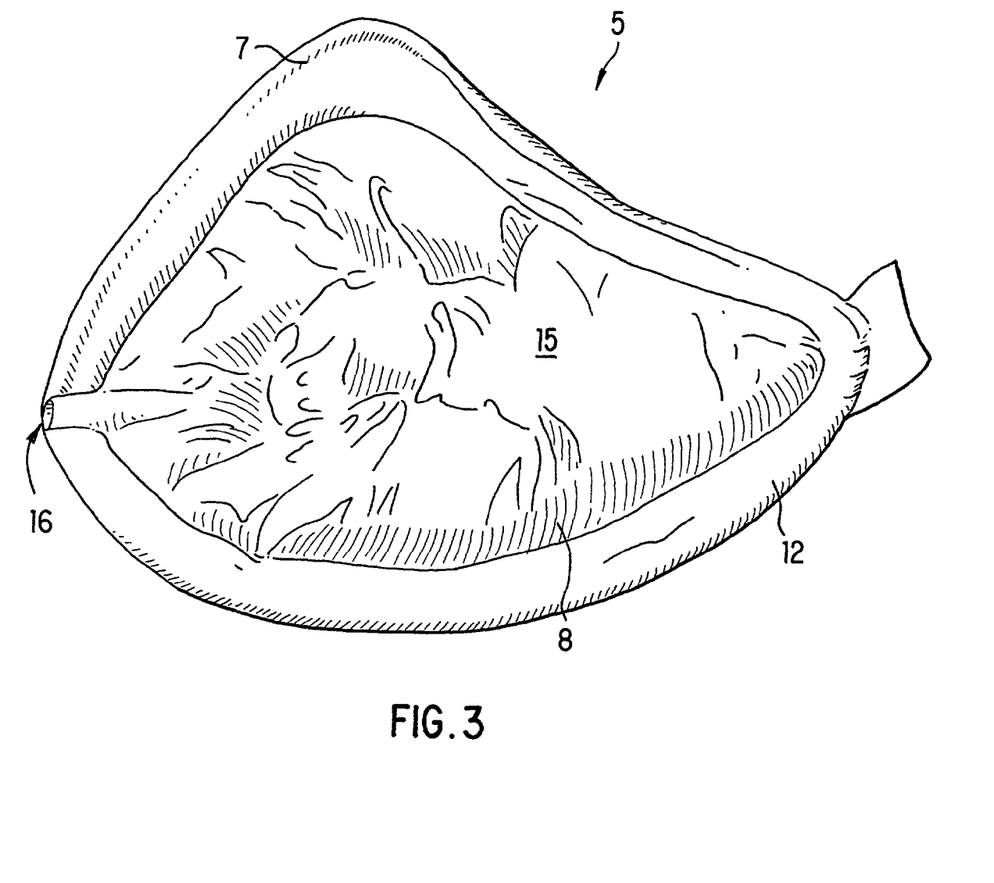
FIG. 3 is a rear or bottom plan view, in partial perspective, of the prosthesis of FIG. 1, illustrating an impression made in and "held" by the self-shaping body portion thereof.
Figure 4:
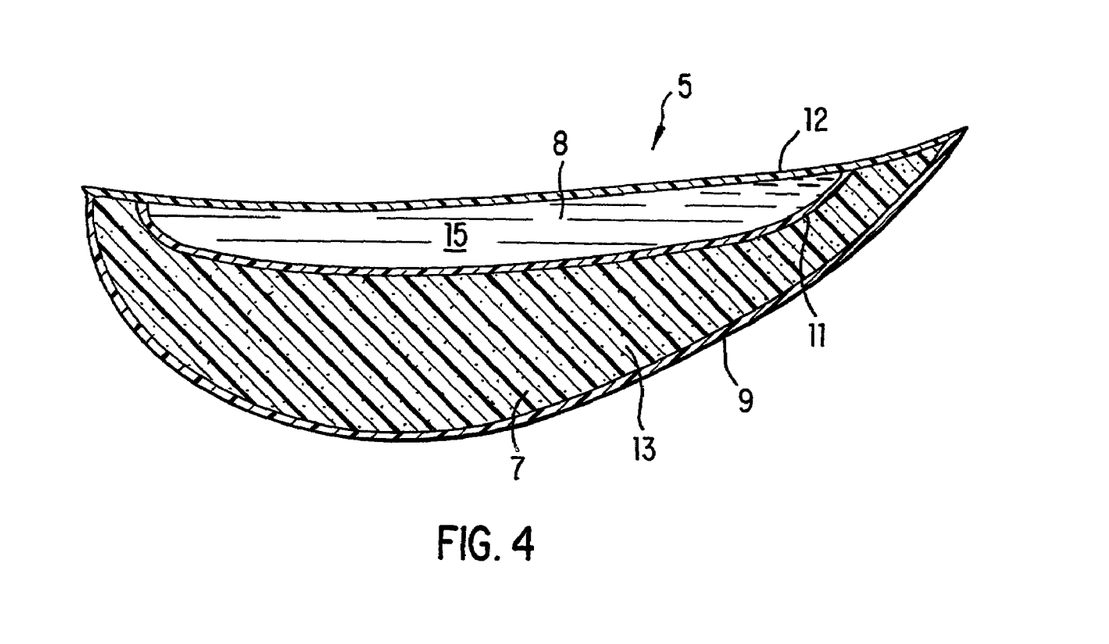
FIG. 4 is a cross-sectional view of the prosthesis of FIG. 1, illustrating the first and second layers or body portions thereof.

Therefore, in one embodiment, the present invention thus provides a breast form having two chambers or shells 7,8 defined by the three polyurethane films 9, 11, 12 joined together along and at their outer peripheries, as illustrated in FIG. 4. The self-shaping material 15 within the second chamber 8 closest to the patient's chest wall is comprised of a dispersion of a silicone fluid and expanded microspheres formulated to give the desired self-molding characteristics. This dispersion has a reduced density of 0.4–0.5 (where water has a specific gravity of 1.0), compared to the specific gravity of an unfilled (no microspheres added) silicone gel of 1.0. The use of this material/dispersion therefore provides the desired self-shaping characteristics while reducing the overall weight of the prosthesis.

So formed, the self-shaping material 15 of the soft inner dispersion can flow into cavities of the patient's chest wall when being worn thereby in order to conform to the contours left in the chest wall after surgery. The "feel" of the breast form is realistic because the outer layer can move to the touch by displacing some part of the soft inner silicone dispersion. The stiffness of the outer gel layer 13 can be varied to the desired parameters by controlling the composition curable elastic material precursor, so that the thickness of the outer layer is decreased as the stiffness thereof is increased. Therefore, the stiffness and thickness of the gel layer 13 can be adjusted to produce the desired "feel" of the prosthesis.

The self-shaping material 15 is preferably blended in a double planetary mixer, a ribbon mixer, or similar mixer types and under a vacuum to remove any dissolved air from the material. The pumping of the material 15 into the second body portion, chamber or envelope 8 of the breast prosthesis should be carried out with a positive displacement pump in a closed configuration that does not allow the material to be otherwise aerated.

Although several embodiments of the invention have been disclosed in the foregoing specification, it is to be understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, but rather is intended to cover such alternatives, modifications, and equivalents as may be included within the spirit and scope of the invention as defined by the appended claims. To this end, one skilled in the art will appreciate that in practicing the present invention, only reasonable and routine experimentation will be required to optimize such variables and conditions as set forth herein.

What is claimed is:

1. A process for manufacturing a two-layer breast prosthesis comprising the steps of:
    a) providing: (i) a first film envelope configured to define a first interior volume; and (ii) a second film envelope joined to the first film envelope along a common side edge to thereby define a second interior volume wherein said second film envelope and said first film envelope share a common interstitial film wall and wherein said first and said second film envelopes further comprise a respective first and a second fill opening extending from the common side edge to the respective first interior volume and second interior volume;
    b) at least partially filling the second interior volume of step a) by passing a curable elastic material precursor through the second fill opening;
    c) at least partially filling the first interior volume of step a) by passing a self-shaping dispersion through the first fill opening, wherein air is removed from the self-shaping dispersion prior to passing the self-shaping dispersion through the first fill opening;
    d) sealing the first and second fill openings; and
    e) curing the elastic material precursor in the second film envelope to provide a two-layer breast prosthesis comprising a cured elastic material layer and an uncured self-shaping layer.

2. The process of claim 1, wherein step e) comprises heat treating the joined first film envelop and second film envelope in a mold having a surface design configured to a desired shape of a breast to thereby cure the elastic material precursor in the second film envelope and to provide a two-layer breast prosthesis having the desired breast shape.

3. The process of claim 1, wherein step d) further comprises sealing the first and second fill openings simultaneously.

4. The process of claim 1, wherein step a) further comprises sealably affixing an interstitial plastic film extending between and to a first and a second exterior plastic film, respectively, along their respective common edges to thereby form the first film envelope and the second film envelope joined to the first film envelope.

5. The process of claim 4, wherein the interstitial plastic film and the first and second exterior films are each comprised of polyurethane.

6. The process of claim 1, wherein the curable elastic material precursor of step b) comprises a silicone gel and a plurality of microspheres.

7. The process of claim 1, wherein the self-shaping dispersion of step c) comprises a silicone oil and a plurality of microspheres.

8. The process of claim 7, wherein the self-shaping dispersion further comprises a thixotropic additive.

9. The process of claim 7, wherein the microspheres have an average particle size in the range of from approximately 40 microns to approximately 125 microns.

10. The process of claim 7, wherein the silicone oil has a viscosity in the range of from approximately 100 CSt to approximately 5000 CSt.

11. The process of claim 10, wherein the silicone oil has a viscosity of approximately 500 CSt.

12. The process of claim 1, wherein step c) comprises pumping the self shaping dispersion through the first opening and into the first interior volume in a closed configuration that does not allow the self shaping dispersion to become aerated.

* * * * *